US00PP26124P2

(12) United States Plant Patent
Schrauwen

(10) Patent No.: US PP26,124 P2
(45) Date of Patent: Nov. 24, 2015

(54) *CHAMAECYPARIS* PLANT NAMED 'VERSENT'

(50) Latin Name: *Chamaecyparis thyoides*
Varietal Denomination: Versent

(71) Applicant: Jean-Pierre Schrauwen, Sprundel (NL)

(72) Inventor: Jean-Pierre Schrauwen, Sprundel (NL)

( * ) Notice: Subject to any disclaimer, the term of this patent is extended or adjusted under 35 U.S.C. 154(b) by 97 days.

(21) Appl. No.: 13/987,817

(22) Filed: Sep. 5, 2013

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

New Plants and Flowers, Sep. 28, 2012.*

* cited by examiner

*Primary Examiner* — Keith Robinson
(74) *Attorney, Agent, or Firm* — Penny J. Aguirre

(57) ABSTRACT

A new cultivar of *Chamaecyparis* named 'Versent' that is characterized by its foliage with growing tips that are blue-green in color with the spring foliage that is silvery blue in color and its narrow and its dwarf, compact, and mounded plant habit.

2 Drawing Sheets

Botanical classification: *Chamaecyparis thyoides.*
Varietal denomination: 'Versent'.

BACKGROUND OF THE INVENTION

The present invention relates to a new and distinct cultivar of *Chamaecyparis thyoides* and will be referred to hereafter by its cultivar name, 'Versent'. 'Versent' represents a new evergreen coniferous shrub grown for landscape use.

The Inventor discovered the new cultivar in 2009 as a naturally occurring branch mutation of *Chamaecyparis thyoides* 'Top Point' (not patented) in a container block at his nursery in Sprundel, The Netherlands.

Asexual propagation of the new cultivar was first accomplished by softwood stem cuttings by the Inventor in Sprundel, The Netherlands in 2009. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Versent' as a unique cultivar of *Chamaecyparis.*

1. 'Versent' exhibits foliage with growing tips that are blue-green in color with the spring foliage that is silvery blue in color.
2. 'Versent' exhibits a dwarf, compact, and mounded plant habit.

The parent plant, 'Top Point', is similar to 'Versent' in having a dwarf and compact plant habit. 'Top Point' differs from 'Versent' in having foliage with spring foliage tips that is less blue in color and in having a more upright plant habit. 'Versent' can be most closely compared to cultivars of *Chamaecyparis thyoide*; 'Little Jamey' (not patented), 'Meth Dwarf' and 'Northern Skies' (all not patented). All are similar to 'Versent' in having a dwarf plant habit. 'Little Jamey' differs from 'Versent' in having a narrowly conical plant habit and in having foliage that is less blue in color. 'Meth Dwarf' differs from 'Versent' in having a conical plant habit and in being slower growing. 'Northern Skies' differs from 'Versent' in having a narrowly upright plant habit and being more dwarf in size.

BRIEF DESCRIPTION OF THE DRAWINGS

The accompanying colored photographs illustrate the overall appearance and distinct characteristics of the new *Chamaecyparis*. The photographs were taken of a plant about 2.5 years in age as grown in a 7.5-liter container in Sprundel, The Netherlands.

The photograph in FIG. 1 provides an overall view of the plant habit of 'Versent'.

Figure 1:
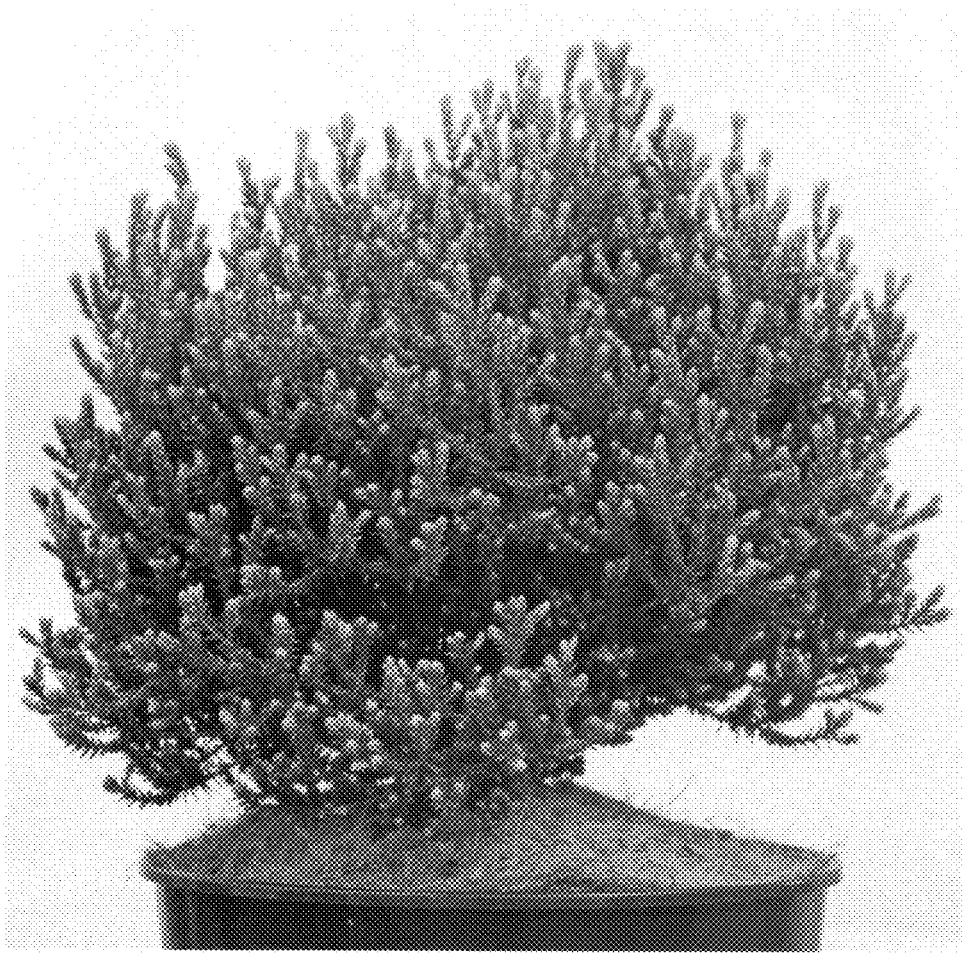
Figure 2:
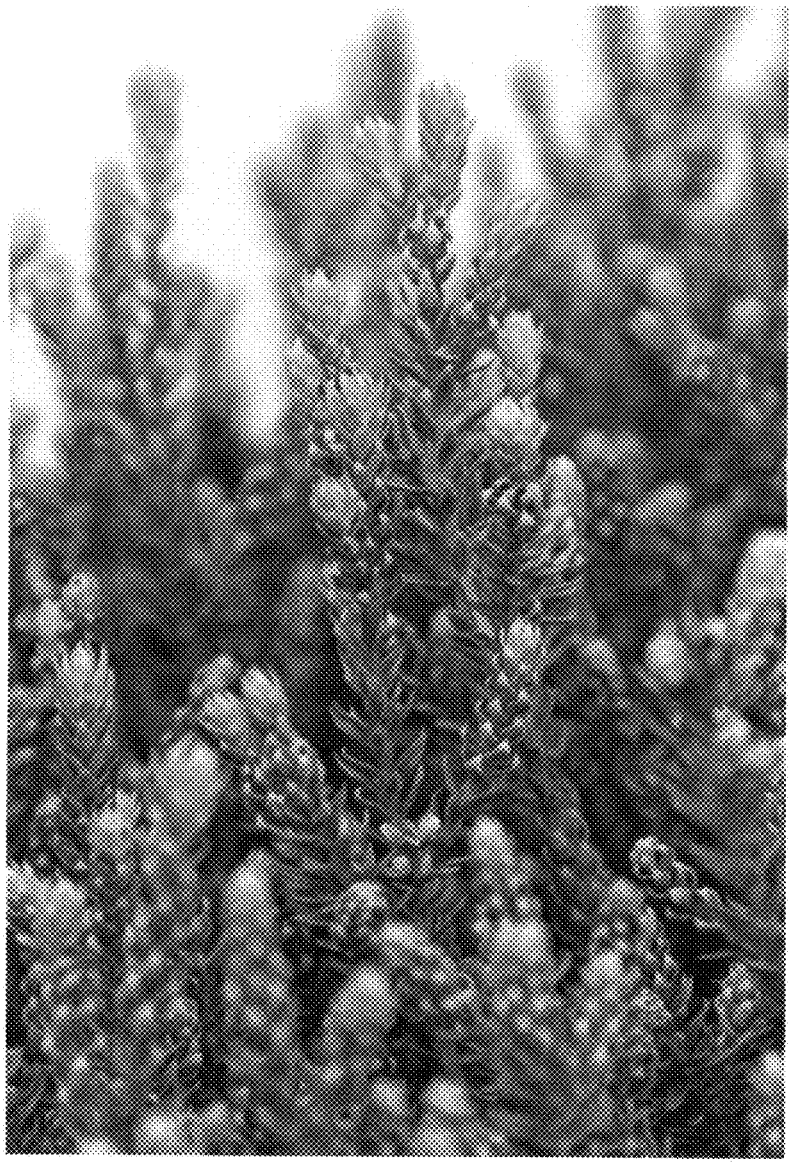

The photograph in FIG. 2 provides a close-up view of the foliage of 'Versent'.

The colors in the photographs are as close as possible with the photographic and printing technology utilized and the values cited in the detailed botanical description accurately describe the colors of the new cultivar.

DETAILED BOTANICAL DESCRIPTION

The following is a detailed description of plants of the new cultivar about 2.5 years in age as grown in 7.5-liter containers in Sprundel, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub (*Chamaecyparis thyoides* is natively a tree, however dwarf forms like the new cultivar are grown as shrubs).

*Growth habit.*—Compact, dwarf, rounded.

*Height and spread.*—An average of 29.9 cm in height and 34.1 cm in spread as a 2.5 year-old plant.

*Cold hardiness.*—At least to U.S.D.A. Zone 6.

*Diseases and pests.*—No susceptibility or resistant to pests and diseases has been observed.

*Root description.*—Fibrous, fine, and shallow, 164D in color. Time required for root development. — An average of six weeks for root initiation, about twelve weeks to produce a young rooted plant.

*Growth rate.*—Moderate.

*Propagation.*—Softwood stem cuttings.

Stem description:

*Shape.*—Rounded.

*Stem size.*—Branch; an average of 15.2 cm in length and 2.5 mm in diameter, branchlet; an average of 3 cm in length and 1.5 mm in diameter.

*Stem surface.*—Branch and branchlet; covered with scale-like leaves, slightly glossy and smooth.

*Branching.*—Very freely branching, basal and lateral branching, 65 lateral branches.

*Branch arrangement.*—Alternate.

*Branch aspect.*—Rounded.

*Internode length.*—18 mm in length.

*Stem color.*—Branch and branchlet; one-year old stems; 148A in color, two-year old stems; N170A in color, older bark; a blend of N199B to between 200C and 200D.

Foliage description:

*Leaf arrangement.*—Alternate.

*Leaf shape.*—Scale-like, ovate.

*Leaf division.*—Simple.

*Leaf base.*—Cuneate.

*Leaf apex.*—Apiculate.

*Leaf venation.*—Not visible.

*Leaf margins.*—Entire.

*Leaf surface.*—Both surfaces smooth, upper surface very glossy and lower surface moderately glossy.

*Leaf color.*—Spring foliage; a blend of 122B and 133A on upper and lower surfaces, young upper surface; 137C and tinged with 133C with base 144C in color, young lower surface; s blend of 136C, 137D and 133C with outer tips a color between 148B to 148C, mature upper surface; a blend of 137A to 143A, mature lower surface; 137B.

*Leaf fragrance.*—Very faintly spreads the fragrance typical of *Chamaecyparis thyroids* when crushed.

*Leaf size.*—An average of 5 mm in length and 2 mm in width.

*Leaf quantity.*—An average of 250 scale-like leaves.

Cone description: No cones have been observed on the plants trialed for data collection.

It is claimed:

1. A new and distinct cultivar of *Chamaecyparis* plant named 'Versent' as herein illustrated and described.

* * * * *